US00PP08461P

United States Patent [19]

Bradford et al.

[11] Patent Number: Plant 8,461

[45] Date of Patent: Nov. 16, 1993

[54] NECTARINE TREE (BRADCRIM)

[76] Inventors: Lowell G. Bradford, 12439 E. Savana Rd.; Norman G. Bradford, 11875 E. Savana Rd., both of Le Grand, Calif. 95333

[21] Appl. No.: 4,417

[22] Filed: Jan. 14, 1993

[51] Int. Cl.[5] ..... A01H 5/00
[52] U.S. Cl. ..... Plt./40.1
[58] Field of Search ..... Plt./40.1

[56] References Cited

U.S. PATENT DOCUMENTS

P.P. 529 6/1942 Lammerts ..... Plt. 42.1
P.P. 974 8/1950 Anderson ..... Plt. 41.3

*Primary Examiner*—James R. Feyrer

[57] ABSTRACT

The present invention relates to a nectarine tree and more particularly to a new and distinct variety broadly characterized by a large size, vigorous, winter hardy, productive and regular bearing tree. The fruit matures under the ecological conditions described approximately the first week in July, with first picking on Jul. 1, 1992. The fruit is uniformly medium in size, nonacidic in flavor, globose in shape, freestone in type, medium firm in texture, and nearly full red in skin color. The variety was developed as a second generation cross using Sun Grand (U.S. Plant Pat. No. 974) nectarine as the seed parent and Robin (U.S. Plant Pat. No. 529) peach as the pollen parent.

1 Drawing Sheet

BACKGROUND OF THE VARIETY

In a continuing effort to improve the quality of fresh market and shipping fruits, we, the inventors, typically hybridize a large number of nectarine and peach seedlings each year. Additionally, we grow a number of open pollinated seeds looking for second generation characteristics. The present invention relates to a new and distinct variety of nectarine tree, which has been denominated varietally as "BRADCRIM". The present variety was developed by us in 1982 by growing an open pollinated seed from an unnamed peach seedling in a cultivated area of our experimental orchard at Bradford Farms near Le Grand, Calif. in Merced County (San Joaquin Valley). This unnamed peach seedling resulted from crossing Sun Grand (U.S. Plant Pat. No. 974) nectarine as a seed parent by Robin (U.S. Plant Pat. No. 529) peach as a pollen parent. Subsequent to origination of the present variety of nectarine tree, we asexually reproduced it by budding and grafting, and such reproduction of plant and fruit characteristics were true to the original plant in all respects.

The fruit produced by the present variety is most similar to its seed grandparent, the Sun Grand (U.S. Plant Pat. No. 974), by producing medium sized, red colored, freestone nectarines that ripen in early July, but is most distinguished therefrom and an improvement thereon by producing fruit that is white in flesh and nonacidic in flavor, instead of yellow in flesh and semi-acidic in flavor.

The present variety is similar to its selected pollen grandparent, the Robin (U.S. Plant Pat. No. 529), by abundantly producing medium sized, mild tasting, white fleshed freestone fruit but is distinguished therefrom and an improvement thereon by producing fruit that ripens about one month later and, most obviously, by being a nectarine instead of a peach.

DRAWING

The accompanying photograph exhibits four whole fruits positioned to display the characteristics of the skin color and form, one fruit divided along the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of eating ripe on Jul. 7, 1992. All major color code designations are by reference to the Inter-Society Color Council, National Bureau of Standards. Common color names are also used occasionally.

TREE

Size: Large.
Vigor: Vigorous.
Growth: Spreading and dense.
Form: Vase formed.
Hardiness: Very hardy.
Production: Very productive.
Bearing: Regular bearer.
Trunk:
- *Size.*—Medium.
- *Texture.*—Medium.
- *Bark Color.*—Grayish brown [61. gy.Br].
- *Lenticels.*—Numerous. Color: Moderate brown [58. m.Br]. Average size: ¼", [6.4 mm.].

Branches:
- *Size.*—Medium.
- *Texture.*—Medium.
- *Color.*—1st year wood: Strong yellow green [117. s.YG] with some grayish yellowish pink [32. gy.yPk] tinting. Older wood: Moderate yellowish brown [77. m.yBr].
- *Lenticels.*—Numerous, very small.

Leaves:
- *Size.*—Large. Average length: 5⅞" [149.2 mm.]. Average width: 1 15/16" [49.2 mm.].
- *Thickness.*—Medium.
- *Form.*—Elliptical.
- *Apex.*—Acuminate.

*Base.*—Acute.
*Surface.*—Smooth.
*Color.*—Dorsal surface: Dark yellowish green [137. d.yG]. Ventral surface: Moderate olive green [125. m.OlG].
*Margin.*—Finely serrate.
Venation.—Pinnately net veined.
*Petiole.*—Average length: ½" [12.7 mm.]. Average thickness: 1/16" [1.6 mm.]. Dorsal color: Moderate yellow green [120. m.YG]. Ventral color: Light yellow green [119. 1.YG].
*Stipules.*—Numerous. Average length: ¼" [6.4 mm.].
*Glands.*—Numbers: 2, to 4 per leaf. Position: Some oppositively and some alternately positioned on petiole and base of blade. Size: Small. Form: Globose. Color: Brilliant yellow green [116. brill.YG].

Flower buds:
*Hardiness.*—Hardy.
*Size.*—Medium.
*Length.*—Medium.
*Form.*—Free.
*Surface.*—Pubescent.

Flowers:
*Blooming period.*—Late as compared with other varieties.
*Size.*—Large.
*Color.*—Moderate pink [5. m.Pk].

FRUIT

Maturity when described: Eating ripe, Jul. 7, 1992.
Date of first picking: Jul. 1, 1992.
Date of last picking: Jul. 10, 1992.
Size: Uniform, medium.
*Average diameter axially.*—2½" [63.5 mm.].
*Average traversely in suture plane.*—2¼" [57.2 mm.].
Form: Uniform, symmetrical, globose.
*Longitudinal section form.*—Slightly oblate, compressed axially.
*Transverse section through diameter.*—Round with a hump on one side of the suture.
Suture: An inconspicuous shallow line extending over the entire surface with a slight depression beyond the pistil point.
Ventral surface: Rounded, lipped throughout on one side.
Lips: Unequal.
Cavity: Flaring, circular, suture showing on one side.
*Depth.*—⅜" [9.5 mm.].
*Breadth.*—⅝" [15.9 mm.].
Base: Slightly truncate, with stem markings typical.
Apex: Most rounded, but some slightly mammiform.
Pistil point: Some apical and some oblique, short in length.
Stem: Medium.
*Average length.*—⅜" [9.5 mm.].
*Average width.*—3/16" [4.8 mm.].
Skin:
*Thickness.*—Thin.
*Texture.*—Medium.
*Tenacity.*—Tenacious to flesh.
*Tendency to crack.*—Slight in wet season.
*Color.*—Dark red [16. d.R] over a pale yellow [89. p.Y] background.

Flesh:
*Color.*—White [263. White] with a very minor amount of moderate red [15. m.R] streaking near the stone.
*Surface of pit cavity.*—Covered with pinkish white [9. pkWhite] fibers.
*Amygdalin.*—Wanting.
*Juice.*—Moderate, rich.
*Texture.*—Medium firm, coarse, meaty.
*Fibers.*—Few, fine.
*Ripens.*—Evenly.
*Flavor.*—Nonacidic and sweet.
*Aroma.*—Pronounce.
*Eating quality.*—Very good.

STONE

Type: Freestone.
Form: Oval.
Base: Straight.
Apex: Acute.
Sides: Equal.
Surface: Irregularly furrowed toward the apex and pitted toward the the base.
Ridges: Jagged toward the base.
Color: Moderate yellowish brown [77. m.yBr].
Pit wall: 3/16" [4.8 mm.] thick.
Tendency to split: Very few observed.
Kernel:
*Form.*—Oval.
*Taste.*—Bitter.
*Viable.*—Yes.
*Average width.*—7/16" [11.1 mm.].
*Average length.*—11/16" [17.5 mm.].
*Pellicle color.*—Light grayish brown [60. 1. gy.Br].
*Amygdalin.*—Abundant.

USE

Market: Home garden, fresh market, and short distance shipping.
Keeping quality: Fair.
Shipping quality: Fair.
Resistance to insects: No unusual susceptibilities noted.
Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is similar to its seed grandparent, the Sun Grand (U.S. Plant Pat. No. 974), by producing medium sized, red colored, medium firm, freestone nectarines that ripen in early July, but is distinguished therefrom and an improvement thereon by producing fruit that is white in flesh and nonacidic in flavor, instead of yellow in flesh and semi-acidic in flavor.

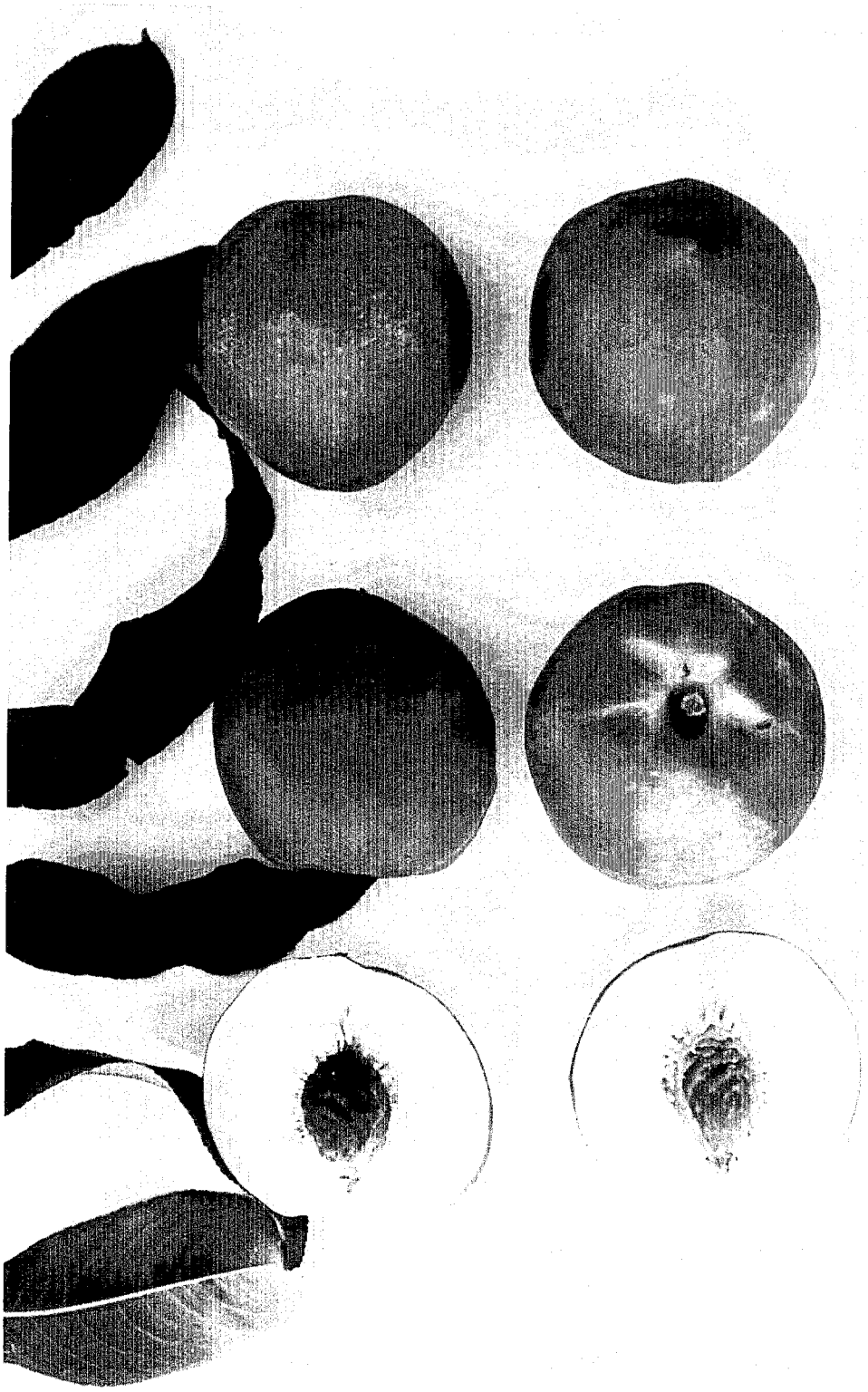

* * * * *